(12) United States Patent
Schultz

(10) Patent No.: US 6,281,240 B1
(45) Date of Patent: Aug. 28, 2001

(54) DIARYLSULFONYLUREAS FOR USE IN TREATING SECRETORY DIARRHEA

(75) Inventor: Bruce D Schultz, Wamego, KS (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/402,874

(22) PCT Filed: Apr. 10, 1998

(86) PCT No.: PCT/US98/07295

§ 371 Date: Jan. 31, 2000

§ 102(e) Date: Jan. 31, 2000

(87) PCT Pub. No.: WO98/44799

PCT Pub. Date: Oct. 15, 1998

Related U.S. Application Data

(60) Provisional application No. 60/043,870, filed on Apr. 10, 1997.

(51) Int. Cl.⁷ .......... A61K 31/18; A61K 31/343; A61K 31/353; A61K 31/381; A61K 31/4045

(52) U.S. Cl. .......... 514/415; 514/443; 514/466; 514/469; 514/470; 514/592; 548/469; 549/52; 549/53; 549/54; 549/55; 549/407; 549/437; 549/462; 549/466; 564/402

(58) Field of Search .......... 514/415, 443, 514/466, 469, 470, 592; 548/469; 549/55, 437, 462, 466, 52, 53, 54, 407; 564/42

(56) References Cited

U.S. PATENT DOCUMENTS

| | | | | |
|---|---|---|---|---|
| 3,202,680 | * | 8/1965 | Korger et al. | 260/347.2 |
| 5,234,922 | * | 8/1993 | Welsh et al. | 514/223.2 |
| 5,254,582 | * | 10/1993 | Boder et al. | 514/469 |

FOREIGN PATENT DOCUMENTS

| | | | |
|---|---|---|---|
| 94/10151 | * | 5/1994 | (WO) . |
| 94/22807 | * | 10/1994 | (WO) . |
| 97/45111 | * | 12/1997 | (WO) . |

* cited by examiner

Primary Examiner—Peter O'Sullivan
(74) Attorney, Agent, or Firm—Paul J. Gaylo

(57) ABSTRACT

This invention provides methods of treating secretory diarrhea or cystic fibrosis in a mammal which comprises administering to a mammal in need thereof an effective amount of diarylsulfonylurea. This invention also describes specific diarylsulfonylureas for use in treating secretory diarrhea or cystic fibrosis.

4 Claims, No Drawings

DIARYLSULFONYLUREAS FOR USE IN TREATING SECRETORY DIARRHEA

PRIORITY CLAIM

This application claims the benefit of U.S. Provisional Patent No. 60/043,870, filed Apr. 10, 1997.

BACKGROUND OF THE INVENTION

The present understanding of the underlying pathophysiological mechanism of acute secretory diarrhea is growing steadily. Secretory diarrhea can accompany gastrointestinal disorders such as inflammatory bowel disease. Acute diarrhea is a world-wide problem, and easily accounts for over a million deaths per year. Medical and pharmacological textbooks generally delineate two classifications for anti-diarrheal medications. The first group are known as astringents. The second group are opium derivatives. While such medications have met with some degree of success, it is an alarming fact that drug development specifically targeting diarrheal disease has been, until recently, almost nonexistent.

Probably the most significant event in the treatment of diarrheal disease in the past one hundred years has been the use of oral glucose-electrolyte solutions. But, there still is a need recognized by world-wide health organizations for continuing effort in diarrhea therapies.

Recent studies of electrolyte transport by intestinal mucosa have provided valuable information concerning the regulation of biochemical events involved in diarrhea. While there is still much refinement work needed, it has now become apparent that a method of treatment of diarrhea would be to control electrolyte transport, particularly chloride secretion.

In chloride secretion, chloride enters the cell across the basolateral membrane on a cotransporter that is coupled to entry of sodium ion ($Na^+$) and potassium ion ($K^+$). The entry step is electrically neutral because the charge on the anion is balanced by the charges on the cations. The cotransporter accumulates chloride ion ($Cl^-$) in the cell at a value greater than that predicted for electrochemical equilibrium. Removal of $Na^+$ from the submucosal solution or addition of a loop diuretic (furosemide or bumetanide) inhibits $Cl^-$ accumulation in the cell, thereby inhibiting $Cl^-$ secretion. Na-K-ATPase in the basolateral membrane maintains the $Na^+$ concentration within the cell lower than that in the submucosal solution; that gradient across the basolateral membrane provides the energy required to pull $Cl^-$ and $K^+$ into the cell. As the pump hydrolyzes adenosine triphosphate, it drives $Na^+$ out of the cell and $K^+$ into the cell; the pump maintains a low intracellular $Na^+$ (approximately 20 mmol/L) and a high intracellular $K^+$ (approximately 150 mmol/L). Thus, by maintaining a low intracellular $Na^+$ concentration, the Na-K-ATPase provides the energy for both $Cl^-$ secretion and $Na^+$ absorption.

Evidence that the $Na^+$ pump is located only on the basolateral side of the cells came from the observation that ouabain, an inhibitor of Na-K-ATPase, inhibits transport only when added to the submucosal surface; addition to the mucosal side had no effect. Studies of ouabain binding also showed localization over the basolateral cell membrane. Although the activity of the $Na^+$ pump is required for transepithelial transport, that activity dose not directly control the rate of transport. Rather, the rate is primarily controlled by the ion channels present in both cell membranes and, possibly, by the $Cl^-$ entry step at the basolateral membrane.

Potassium, which enters the cell on the $Na^+$ pump (and may also do so in the $Na^+$—$K^+$—$Cl^-$ entry step), must exit across the basolateral membrane because there is very little $K^+$ secretion in most secretory epithelia. $K^+$ accumulates in the cell above electrochemical equilibrium and thus can flow passively out of the cell through basolateral $K^+$ channels.

The patch-clap technique, combined with studies of transepithelial current and isotope fluxes, revealed that $K^+$ can exit across the basolateral membrane through at least two types of $K^+$ channels, those gated by $Ca^{2+}$ and those gated by some other factor, probably cAMP.

This exit of $K^+$ across the basolateral membrane plays two important physiologic roles. First, it maintains a negative intracellular voltage, which is important for driving $Cl^-$ exit across the apical membrane. Second, it prevents cell swelling, which would otherwise result from entry of $K^+$. Thus, the activity of the basolateral $K^+$ channels contributes to the overall rate of transport.

The apical membrane of airway epithelial cells contains $Cl^-$ channels, which, when activated, provide pores through which $Cl^-$ can move passively, down a favorable electrochemical gradient into the mucosal solution. Recent work indicates that the cystic fibrosis transmembrane conductance regulator (CFTR) is the $Cl^-$ channel responsible for cAMP-mediated $Cl^-$ secretion. Addition of a hormone, such as a beta-adrenergic agonist, or a toxin, such as cholera toxin, leads to an increase in cAMP, activation of cAMP-dependent protein kinase, and phosphorylation of the CFTR $Cl^-$ channel, which causes the channel to open. An increase in cell $Ca^{2+}$ can also activate different apical membrane channels. Phosphorylation by protein kinase C can either open or shut $Cl^-$ channels in the apical membrane.

Accordingly a primary objective of the present invention is to develop an effective treatment for secretory diarrhea. Another objective of the present invention is to develop an effective treatment for secretory diarrhea that involves the electrolyte transport mechanism, which is the underlying cause of secretory diarrhea.

Another objective of the present invention is to provide a treatment for secretory diarrhea, which involves use of agents that block the CFTR chloride channel, these agents include sulfonylureas and related agents that have been called potassium channel blockers and openers; prevention of the chloride channel transfer mechanism will prevent diseases involving secretion, such as diarrhea.

Another objective of the present invention is to provide a pharmaceutically acceptable composition, especially adapted for oral dosage, which contains some of the active compounds of the present invention in a pharmaceutically acceptable oral dosage carrier.

The method and manner of accomplishing each of the above objectives, as well as others, will become apparent from the detailed description of the invention which follows hereinafter.

The disclosed invention relates to a method of treating secretory diarrhea. The method involves administering active compounds which interfere with cellular mechanism of electrolyte transport which usually accompanies secretory diarrhea. In particular, by administering the compounds which are CFTR chloride channel blockers, the chloride secretion phenomenon usually accompanying secretory diarrhea is blocked. As a result the disease is effectively treated.

SUMMARY OF THE INVENTION

This invention provides methods of treating secretory diarrhea in a mammal which comprises administering to a mammal in need thereof an effective amount of a diarylsulfonylurea of Formula I

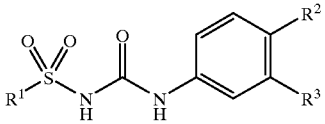

wherein:
R$^1$ is selected from the group consisting of

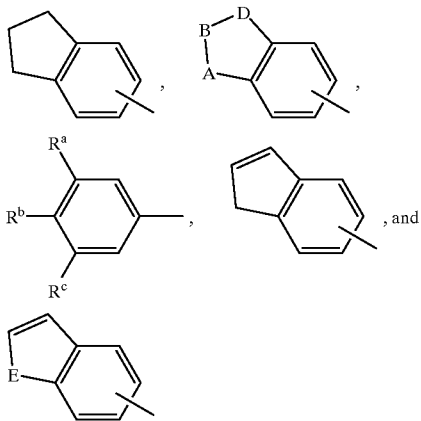

wherein:
E is nitrogen, sulfur, or oxygen;
where A is —O—, —S(O)$_n$—, —CH$_2$S(O)$_n$—, —NR—, —CH$_2$—, —CH$_2$CH$_2$—, or —CH$_2$O—;
D is —CH$_2$—, —S(O)$_n$—, —NR—, —CH$_2$S(O)$_n$—, or —O—;
B is —CH$_2$—, —O—, —S(O)$_n$—, or —NR—;
R is methyl or ethyl;
n is 0–2;
provided that at least one of A, B, and D is not —S(O)$_n$— or —CH$_2$S(O)$_n$—; and
R$^a$, R$^b$, and R$^c$ are independently selected from the group consisting of hydrogen, halo, C$_1$–C$_3$ alkyl, C$_1$–C$_3$ alkoxy, and trifluoromethyl;
or one of R$^a$, R$^b$, and R$^c$ is C$_2$–C$_8$ alkenyl, another of R$^a$, R$^b$, and R$^c$ hydrogen or hydroxy, and the other of R$^a$, R$^b$, and R$^c$ is hydrogen;
R$^4$ and R$^5$ are independently selected from the group consisting of hydrogen and C$_1$–C$_3$ alkyl;
R$^3$ is hydrogen, halo, C$_1$–C$_3$ alkyl, or trifluoromethyl; and
R$^2$ is halo, C$_1$–C$_3$ alkyl, or trifluoromethyl;
or a pharmaceutically acceptable salt or solvate thereof.

DETAILED DESCRIPTION AND PREFERRED EMBODIMENTS

As used herein, the term "halo" refers to fluoro, chloro, bromo, and iodo.

Preferred compounds of the instant invention are those of Formula I wherein:
R$^1$ is selected from the group consisting of 2,3-dihydrobenzofuryl, indanyl, indenyl, benzofuryl, indolyl, indolinyl, halo-substituted phenyl, and alkyl-substituted phenyl;
R$^2$ is chloro, bromo, methyl, or trifluoromethyl;
R$^3$ is hydrogen, chloro, bromo, methyl, or trifluoromethyl; and
R$^4$ and R$^5$ are independently hydrogen or methyl.

U.S. Pat. No. 5,234,922, issued Aug. 10, 1993, the entire contents of which are herein incorporated by reference, describes the use of alkylsulfonylureas for the treatment of secretory diarrhea. Such compounds, especially tolbutamide and glibenclamide, are commonly employed as hypoglycemic agents. This patent also teaches the use of potassium channel openers, such as diazoxide, lemakalim, and minoxidil sulfate, for treating secretory diarrhea.

The present invention employs diarylsulfonylureas. Some diarylsulfonylureas have been reported as being active antitumor agents. e.g., U.S. Pat. No. 5,169,860, of F. Mohamadi and M. Spees, issued Dec. 8, 1992; U.S. Pat. No. 4,845,128 of Harper, et al., issued Jul. 4, 1989; U.S. Pat. No. 5,110,830 of Harper, et al., issued May 5, 1992; U.S. Pat. No. 5,116,874 of G. A. Poore, issued May 26, 1992; U.S. Pat. No. 5,216,026, of J. Howbert, issued Jun. 1, 1993; U.S. Pat. No. 5,216,027, of J. E. Ray, et al., issued Jun. 1, 1993; U.S. Pat. No. 5,302,724, issued Apr. 12, 1994; U.S. Pat. No. 5,234,955, issued Aug. 10, 1993; U.S. Pat. No. 5,116,874, issued May 26, 1992; U.S. Pat. No. 5,594,028, issued Jan. 14, 1997; U.S. Pat. No. 5,262,440, issued Nov. 16, 1993; U.S. Pat. No. 5,254,582, issued Oct. 19, 1993; U.S. Pat. No. 5,565,494, issued Oct. 15, 1996; and U.S. Pat. No. 5,354,778, issued Oct. 11, 1994. All of these patents are herein incorporated in their entirety. It is believed all of these diarylsulfonylureas will be useful in the treatment of secretory diarrhea.

The diarylsulfonylureas of Formula I can be prepared by any number of methods known in the literature. Generally, these methods involve either the reaction of a sulfonamide with an isocyanate or a reaction of a sulfonylcarbamate with an appropriately-substituted aniline.

A preferred process for preparing a compound of Formula I comprises reacting a sulfonylisocyanate of Formula III

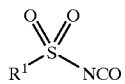

with an aniline derivative of Formula IV

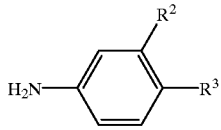

wherein R$^1$, R$^2$, and R$^3$ are the same as previously defined, generally in the presence of a base. Any suitable basic material, such as sodium hydroxide, potassium hydroxide, lithium hydroxide, sodium methoxide, sodium hydride and the like, can be used.

The reaction between compounds III and IV is usually performed using equimolar amounts of the two reactants, although other ratios are operative. The reaction is preferably carried out in a solvent which is nonreactive under the reaction conditions such as benzene, toluene, acetonitrile, diethyl ether, tetrahydrofuran, dioxane, methylene chloride, or most preferably acetone.

The reaction can be carried out at temperatures from about 0° C. up to about 100° C. At the preferred temperature range of from about 20° C. to about 30° C., the reaction produces a strong exotherm and the reaction is usually complete within one hour. The product thus obtained can be recovered by filtration and can be purified, if desired, by any number of methods known to those skilled in the art, such as chromatography or crystallization.

An alternative process for preparing a compound of Formula I comprises reacting an appropriately substituted sulfonamide of Formula V

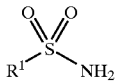

V with an isocyanate of Formula VI

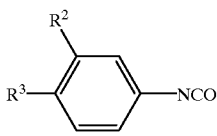

VI to provide the corresponding compound of Formula II.

The reaction is generally performed in a mixture of water and a water-miscible, non-reactive solvent such as tetrahydrofuran or acetone in the presence of an acid scavenger such as sodium hydroxide, potassium hydroxide, lithium hydroxide, sodium methoxide, sodium hydride and the like. Generally, an equimolar or slight molar excess of VI is employed, although other ratios are operative. Usually, the amount of base used is approximately equimolar to the amount of V. The reaction is generally carried out from about 0° C. up to about 100° C. At the preferred temperature of about 20° C. to about 30° C., the reaction is usually complete within about three hours.

A preferred process for preparing a compound of Formula II involves reacting a sulfonamide of Formula V with an alkyl haloformate of the formula $XCOOR^9$, where X is bromo or chloro and $R^9$ is $C_1$–$C_3$ alkyl, to provide the carbamate of Formula VII and then reacting it with an aniline derivative of Formula IV to provide the corresponding product I

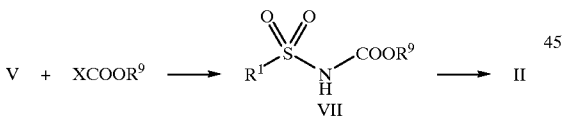

The transformation of V into VII is usually accomplished in a non-reactive solvent, such as acetone or methyl ethyl ketone, in the presence of an acid scavenger, such as an alkali metal carbonate, for example potassium carbonate. A molar excess of the haloformate is usually added, although other ratios are operative. The reaction mixture is heated to a temperature from about 30° C. up to the reflux temperature of the mixture for a period of about 1–6 hours to provide the desired intermediate VII. Intermediate carbamate VII and the substituted aniline IV are then heated together in an inert high-boiling solvent, such as dioxane, toluene, or diglyme, at temperatures from about 50° C. up to the reflux temperature of the mixture to provide the desired product I.

Intermediates II, IV, V, and VI and other reagents required for other methods of preparation, are commercially available, or can be prepared by methods known in the art. See, e.g. J. A. Aikins and E. V. P. Tao, European Patent Publication No. 254,577, published Jan. 27, 1988.

EXAMPLE 1

Synthesis of N-[[(4-chlorophenyl)amino]carbonyl]-indene-5-sulfonamide (A) and N-[[(4-chlorophenyl)amino]carbonyl]-indene-6-sulfonamide (B)

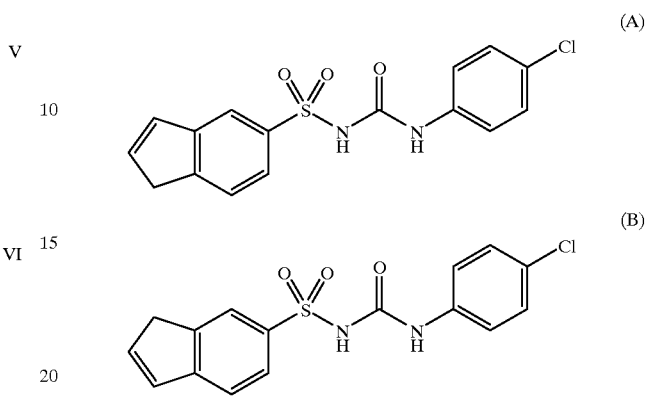

A. Preparation of 1-Hydroxy-5-indanesulfonamide

To a stirred solution of 1-keto-5-indanesulfonamide (6.3 g, 30 mmol), in 120 ml of 50% aqueous methanol at 0° C. was added $NaBH_4$ (1.1 g, 30 mmol) in several portions. The cooling bath was removed and the mixture allowed to stir at room temperature for 30 minutes. After removal of the methanol in vacuo, the residue was extracted with ethyl acetate (4×75 ml) and the combined organic phase dried ($Na_2SO_4$). Filtration, followed by evaporation of the solvent, gave 5.4 g (84%) of product as a white solid.

B. Preparation of Indene-6-sulfonamide

A mixture of the product produced supra (3.07 g, 14.5 mmol) and p-toluenesulfonic acid monohydrate (276 mg, 1.5 mmol) in 1,2-dichloroethane (200 ml) was heated at reflux for 1 hour. After cooling, the solution was washed with 5% $NaHCO_3$ (1×100 ml) and water (1×100 ml) and dried ($Na_2SO_4$). Concentration in vacuo gave a yellow solid which was chromatographed on silica gel (20–40% EtOAc/hexane) to give 1.9 g (65%) of the product as a white solid.

C. Preparation of N-[[(4-chlorophenyl)amino]-carbonyl]-indene-5-sulfonamide (A) and N-[[(4-chlorophenyl)amino]carbonyl]-indene-6-sulfonamide (B)

A solution of indene-6-sulfonamide (2.1 g, 10.8 mmol) in acetone (5 ml) and 1N aqueous sodium hydroxide (10.8 ml, 10.8 mmol) was treated dropwise with a solution of p-chlorophenylisocyanate (2.0 g, 12.8 mmol) in 5 ml acetone over 20 minutes. After stirring 2 hours, the insoluble bis(p-chlorophenyl)urea was removed by filtration and the resulting clear solution neutralized by the addition of 1N aqueous HCl (10.8 ml, 10.8 mmol). The slurry was stirred 30 minutes, filtered and washed with $H_2O$ (100 ml) and ether (50 ml). Drying gave 3.4 g of solid, which was suspended in 100 ml of $H_2O$ and treated with 1N aqueous NaOH (20 ml). The insoluble material was removed by filtration through a pad of CELITE™. Neutralization of the filtrate with 20 ml of 1N aqueous HCl precipitated a solid which was collected by filtration and dried to yield 2.21 g (59%) of the product. NMR studies indicated the product to be a 7:5 mixture of the 6- and 5-indenylsulfonyl isomers. These isomers may be separated, if desired, by techniques which are well known in the art.

Analysis of the product mixture gave the following results:

mp=159–161° C.; $R_f$ (1/9 MeOH/CHCl$_3$)=0.36; $^1$H NMR (300 MHz, d$_6$-DMSO): A: δ3.55 (s, 2H, C$\underline{H}_2$), 6.90 (d, 1H, J=5.6 Hz, C$\underline{H}$), 7.05 (m, 1H, C$\underline{H}$), 7.25–7.35 (m, 4H, Ar—$\underline{H}$), 7.60 (d, 1H, J=8.0 Hz, Ar—$\underline{H}$), 7.84(d, 1H, J=8.0 Hz, Ar—$\underline{H}$), 8.02 (s, 1H, Ar—$\underline{H}$), 8.96 (bs, 1H, exchanges with D$_2$O, N$\underline{H}$), 10.82 (bs, 1H, exchanges with D$_2$O, N$\underline{H}$); B δ3.52 (s, 2H, C$\underline{H}_2$), 6.78 (d, 1H, J=5.6 Hz, C$\underline{H}$), 7.05 (m, 1H, C$\underline{H}$), 7.25–7.35 (m, 4H, Ar—$\underline{H}$), 7.70 (d, 1H, J=8.0 Hz, Ar—$\underline{H}$), 7.78 (d, 1H, J=8.0 Hz, Ar—$\underline{H}$), 7.98 (s, 1H, Ar—$\underline{H}$), 8.95 (bs, 1H, exchanges with D$_2$O, NH), 10.82 (bs, 1H, exchanges with D$_2$O, N$\underline{H}$); IR(KBr) 3367, 3274, 1716, 1606, 1545, 1498, 1464, 1341, 1148, 1033, 922, 696 and 587 cm$^{-1}$; UV(EtOH)) λmax(e) 251.8 (29988) and 204.8 (37094) nm; FDMS (MeOH) m/e 348, 350 (M$^+$).

Analysis for C$_{16}$H$_{13}$ClN$_2$O$_3$S: Theory: C, 55.09; H, 3.76; N, 8.03. Found: C, 55.19; H, 3.72; N, 7.84.

EXAMPLE 2

Preparation of N-[[(4-chlorophenyl)amino] carbonyl]-2-benzofuransulfonamide

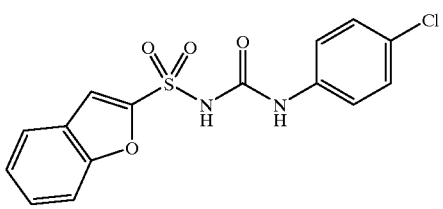

To a solution of benzofuran (4.55 g, 38.5 mmol) in 100 ml of anhydrous tetrahydrofuran under a nitrogen atmosphere at −78° C. was added a 1.3 M hexanes solution of n-butyllithium (29.6 ml, 38.5 mmol). The reaction was warmed to 0° C. and stirred for 30 minutes. Sulfur dioxide gas was bubbled through this mixture for 20 minutes at 0° C. and the reaction was concentrated under vacuum. The residue was dissolved in 100 ml of water, to which were added 304 millimoles of sodium acetate and 100 millimoles of hydroxylamine-O-sulphonic acid. This reaction was stirred at room temperature for 1.5 hours. The mixture was diluted with 200 ml of water, and the aqueous layer was separated and poured into 600 ml of diethyl ether. The ether layer was extracted with 1 N sodium hydroxide (3×100 ml). The combined aqueous extract was acidified with about 300 ml of 1 N hydrochloric acid, and then extracted with methylene chloride. The combined methylene chloride extract was dried with anhydrous sodium sulfate, filtered, and concentrated under vacuum to provide 2.3 g of 2-benzofuransulfonamide.

To a solution of sulfonamide (11.7 mmol) dissolved in 10 ml of acetone was added 1 N aqueous sodium hydroxide (11.7 ml, 11.7 mmol). The mixture was stirred at room temperature for 10 minutes. A solution of the 4-chlorophenylisocyanate (11.7 mmol) dissolved in 10 ml of acetone was added dropwise to this mixture. The reaction was stirred overnight, then acidified with 11.7 ml (11.7 mmol) of 1 N aqueous hydrochloric acid. The precipitated N-aryl-N'-arylsulfonylurea was filtered under vacuum and purified by flash chromatography to obtain 2 grams of the title product as a solid. W. C. Still, et al., *Journal of Organic Chemistry*, 43:2923 (1978).

$^1$H NMR (CD$_3$SOCD$_3$): δ9.23 (s, 1 H), 7.87 (d, J=9 Hz, 1 H), 7.82 (s, 1 H), 7.78 (d, J=9 Hz, 1 H), 7.58 (dd, J=9, 9 Hz, 1 H), 7.46 (m, 1 H), 7.44 (d, J=9 Hz, 2 H), 7.32 (d, J=9 Hz, 2 H).

Analysis for C$_{15}$H$_{11}$ClN$_2$O$_4$S: Theory: C, 51.36; H, 3.16; N, 7.99. Found: C, 51.39; H, 3.25; N, 7.89.

EXAMPLE 3

Preparation of N-[[(4-methylphenyl)amino] carbonyl]-2-benzofuransulfonamide

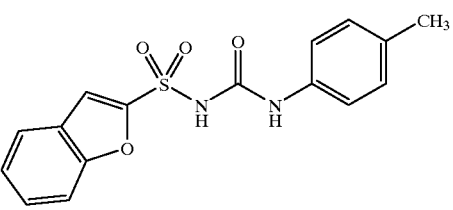

2-Benzofuransulfonamide (7.6 mmol), prepared as described in Example 2, was reacted with 4-methylphenylisocyanate (7.6 mmol) as described in Example 2 to obtain 1.6 g of the title product as a solid.

$^1$H NMR (CD$_3$SOCD$_3$): δ8.91 (s, 1 H), 7.87 (d, J=8 Hz, 1 H), 7.81 (s, 1 H), 7.76 (d, J=8 Hz, 1 H), 7.57 (dd, J=8, 8 Hz, 1 H), 7.42 (dd, J=8, 8 Hz, 1 H), 7.28 (d, J=9 Hz, 2 H), 7.07 (d, J=9 Hz, 2 H), 2.23 (s, 3 H).

Analysis for C$_{16}$H$_{14}$N$_2$O$_4$S: Theory: C, 58.70; H, 4.27; N, 8.48. Found: C, 58.45; H, 4.33; N, 8.47.

EXAMPLE 4

Preparation of N-[[(3,4-dichlorophenyl)amino] carbonyl]-2-benzofuransulfonamide

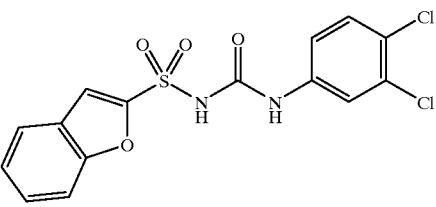

2-Benzofuransulfonamide (7.6 mmol), prepared as described in Example 2, was reacted with 3,4-dichlorophenylisocyanate (7.6 mmol) as described in Example 2 to obtain 2.4 g of the title product as a solid.

$^1$H NMR (CD$_3$SOCD$_3$): δ9.43 (s, 1 H), 7.88 (d, J=8 Hz, 1 H), 7.85 (s, 1 H), 7.80 (m, 1 H), 7.76 (m, 1 H), 7.59 (dd, J=6, 8 Hz, 1 H), 7.52 (d, J=8 Hz, 1 H), 7.45 (dd, J=6, 8 Hz, 1 H), 7.35 (dd, J=3, 6 Hz, 1 H).

Analysis for C$_{15}$H$_{10}$Cl$_2$N$_2$O$_4$S: Theory: C, 46.77; H, 2.63; N, 7.27. Found: C, 46.78; H, 2.63; N, 7.24.

EXAMPLE 5

Preparation of N-[[(4-chlorophenyl)amino]carbonyl]- 1H-indole-6-sulfonamide

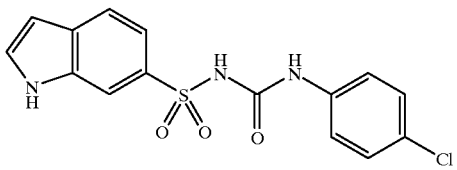

To a solution of 4-chloro-3-nitrophenyl-sulfonamide (12 g, 51 mmol) dissolved in 50 ml of anhydrous dimethylformamide, was added 13.1 g (116 mmol) of ethylcyanoacetate and 10.5 g (76 mmol) of anhydrous potassium carbonate. This mixture was heated at 110° C. for 3 hours, cooled to room temperature, and added to ice water containing 8 ml of concentrated sulfuric acid. The mixture was extracted with ethyl acetate (3×200 ml), and the combined organic layer was back extracted with 200 ml of water. The organic layer was dried over anhydrous sodium sulfate, filtered, and concentrated under vacuum. Purification by a preparative high pressure liquid chromatogram (Waters Prep 500 A) with 55% ethyl acetate in hexanes on a silica gel cartridge. The product was added to 45 ml of 50% aqueous acetic acid containing 3 ml of concentrated sulfuric acid and refluxed for 12 hours. The reaction was cooled to room temperature and added to 400 ml water. This mixture was extracted with ethyl acetate (3×100 ml). The combined organic layer was dried with anhydrous sodium sulfate, filtered, and concentrated under vacuum. The residue was crystallized from 40 ml of ethyl acetate, 3 ml of ethanol and 1 ml of hexanes to obtain 6.9 g of 3-nitro-4-(2-acetonitrile) phenyl sulfonamide. This material was dissolved in 40 ml of ethanol containing 3 g of 5% palladium on activated carbon. This mixture was placed in a Parr Hydrogenation apparatus with 60 p.s.i. of hydrogen at 40° C. for 3 hours. This mixture was filtered, the filtrate concentrated under vacuum, and the residue recrystallized from 20 ml of ethyl acetate and 10 ml of ethanol to obtain 2.4 g of 6-indolesulfonamide. The sulfonamide (6.1 mmol) was reacted with 4-chlorophenylisocyanate (6.1 mmol) as described in Preparation 2 supra to obtain 1.1 g of the title product as a solid.

$^1$H NMR (CD$_3$SOCD$_3$): δ11.68 (s, 1 H), 8.90 (s, 1 H), 8.10 (d, J=2 Hz, 1 H), 7.72 (d, J=9 Hz, 1 H), 7.66 (d, J=3 Hz, 1 H), 7.58 (dd, J=3, 9 Hz, 1 H), 7.40 (d, J=9 Hz, 2 H), 7.28 (d, J=9 Hz, 2 H), 6.60 (d, J=2 Hz, 1 H).

Analysis for C$_{15}$H$_{12}$ClN$_3$O$_3$S: Theory: C, 51.51; H, 3.46; N, 12.01. Found: C, 51.24; H, 3.67; N, 11.72.

EXAMPLE 6

Preparation of N-[[(4-chlorophenyl)amino]carbonyl] benzo[B]thiophene-2-sulfonamide

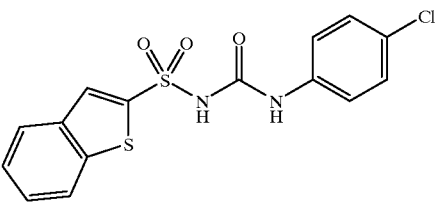

To a solution of 13.4 g (100 mmol) of benzothiophene, dissolved in 50 ml anhydrous diethyl ether, was added 62.5 ml of a 1.6 M hexanes solution of n-butyllithium (100 mmol). The reaction mixture was refluxed for 4 hours and then cooled to about −20° C. Sulfuryl chloride (16.1 ml, 200 mmol) was added dropwise. This suspension was stirred at ambient temperature overnight and then added to 75 ml of ice water. The ether layer was dried over anhydrous sodium sulfate, filtered, and concentrated under vacuum. The residue was added to 100 ml of concentrated ammonium hydroxide and the suspension was warmed to 55° C. The solution was diluted with 200 ml of water and stirred at ambient temperature for several hours. Product was collected by filtration under vacuum. The residue was suspended in 150 ml toluene and filtered to provide 9.2 g of 2-benzo[B]thiophenesulfonamide. The sulfonamide (25 mmol) was reacted with 4-chlorophenylisocyanate (27 mmol) as described in Preparation 2 above to obtain 8.7 g of the title product as a solid.

$^1$H NMR (CD$_3$SOCD$_3$): δ9.12 (s, 1 H), 8.22 (s, 1 H), 8.10 (m, 2 H), 7.50 (m, 2 H), 7.44 (d, J=9 Hz, 2 H), 7.32 (d, J=9 Hz, 2 H).

Analysis for C$_{15}$H$_{11}$ClN$_2$O$_3$S$_2$: Theory: C, 49.11; H, 3.02; N, 7.64. Found: C, 49.36; H, 3.09; N, 7.54.

EXAMPLE 7

Preparation of 3,4,5-trichlorobenzenesulfonamide

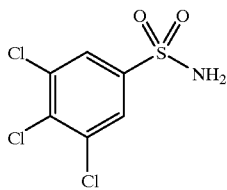

3,5-Dichloro-4-aminobenzenesulfonamide (12.1 g, 50.2 mmol) was added to 150 ml of concentrated hydrochloric acid; the thick suspension was cooled to 0° C. and, with vigorous stirring, treated with a solution of sodium nitrite (4.2 g, 60.9 mmol) in 20 ml of water, dropwise, over 15 min; the resulting orange diazonium salt mixture was slowly poured into a beaker containing cuprous chloride (12.4 g, 125.5 mmol) and 100 ml of concentrated hydrochloric acid at 0° C. (the reaction mixture foams and must be mechanically stirred). The stirred reaction mixture was warmed to room temperature for 1 h and then heated at 70° C. for 30 min. After cooling, the reaction mixture was extracted with methylene chloride (3×200 ml). The combined organic layers were dried over sodium sulfate, filtered and concentrated to give 9.89 g of the product as a yellow solid. Silica gel flash chromatography (30% ethyl acetate/hexane) afforded 8.13 g (62%) of the sulfonamide as a white solid.

Analysis of the product gave the following results: mp=190–191° C.; $R_f$(1:1 EtOAc/hexane)=0.57; $^1$H NMR (300 MHz, $d_6$-DMSO) δ7.68 (bs, 2H, exchanges with $D_2O$, N$\underline{H}_2$) and 7.97 (s, 2H, Ar—$\underline{H}$); IR(KBr) 3308, 2969, 1623, 1529, 1458, 1292, 1163, 1111, 976 and 842 cm$^{-1}$; FDMS (DMSO) m/e=259, 261, 263 (M$^+$).

Analysis for $C_6H_4Cl_3N_1O_2S_1$: Theory: C, 27.66; H, 1.55; N, 5.38. Found: C, 27.87; H, 1.51; N, 5.09.

EXAMPLE 8

Preparation of N-[[(4-chlorophenyl)amino]carbonyl]-3,4,5-trichlorobenzenesulfonamide

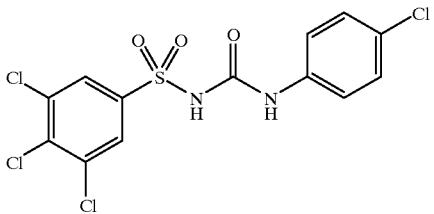

The method of Example 2 was followed using 3,4,5-trichlorobenzenesulfonamide (2.6 g, 10 mmol) as prepared in Example 7, supra, 1N sodium hydroxide solution (10 ml, 10 mmol) and p-chlorophenyl isocyanate (1.7 g, 11 mmol) to yield 3.59 g (87%) of product.

Analysis of the product gave the following results: mp=193–195° C.; $R_f$(5/95 MeOH/CH$_2$Cl$_2$)=0.24; $^1$H NMR (300 MHz, $d_6$-DMSO) δ6.58 (s, 2H, exchanges with $D_2O$, N$\underline{H}_2$), 7.31 (d, 2H, J=8.9 Hz, Ar-$\underline{H}$), 7.37 (d, 2H, J=8.9 Hz, Ar—$\underline{H}$) 7.73 (s, 2H, Ar—$\underline{H}$), 9.09 (s, 1H, exchanges with $D_2O$, N$\underline{H}$) and 10.7 (bs, 1H, exchanges with $D_2O$, N$\underline{H}$); IR(KBr) 3496, 3470, 3375, 3294, 1700, 1622, 1595, 1524, 1451, 1401, 1341, 1166, 1041, 925 and 672 cm$^{-1}$; FDMS (DMSO) m/e 392, 394, 396 (M$^+$).

Analysis for $C_{13}H_{10}Cl_3N_3O_3S$: Theory: C, 39.56; H, 2.55; N, 10.65. Found: C, 39.64; H, 2.55; N, 10.33.

EXAMPLE 9

Preparation of N-[[(3,4-dichlorophenyl)amino]carbonyl]-2,3-dihydro-1-methyl-1H-indole-5-sulfonamide

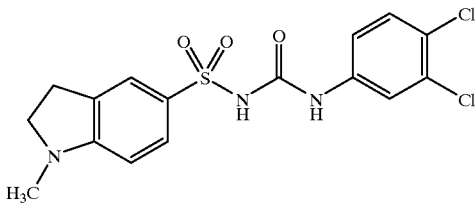

Ethyl-indoline-1-carboxylate-5-sulfonamide

To a flask containing chlorosulfonic acid (125 ml, 1.9 moles) was added 70.5 grams of ethyl-indoline-1-carboxylate (0.37 mole) in portions under nitrogen purge with vigorous stirring over 20 minutes. The ethyl-indoline-1-carboxylate was prepared using techniques known in the art. See, e.g., B. de Oliveira, et al., *Journal of the Chemical Society, Perkin Transactions I*, 1477 (1977). After 90 minutes at room temperature the reaction mixture was carefully poured onto 500 g crushed ice and extracted with dichloromethane (3×200 ml). The combined organic extracts were dried by filtration through calcium sulfate and then evaporated. The resulting crude sulfonyl chloride was stirred with 500 ml of ammonium hydroxide for 2 hours. Filtration, followed by washing (500 ml of water followed by 500 ml of diethyl ether) and vacuum drying gave the product sulfonamide as a white solid. Yield=80.4 g (81%).

Analysis of the product gave the following results: mp=164–165° C.; $R_f$(1/1 ethyl acetate/hexanes)=0.28; $^1$H NMR (300 MHz, $d_6$-DMSO) δ1.26 (t, 3H, J=7.1 Hz, CH$_2$C$\underline{H}_3$), 3.13 (t, 2H, J=8.7 Hz, CH$_2$C$\underline{H}_2$), 3.97 (t, 2H, J=8.7 Hz, CH$_2$C$\underline{H}_2$), 4.19 (q, 2H, J=7.1 Hz, C$\underline{H}_2$CH$_3$), 7.18 (s, 2H, exchanges with $D_2O$, $SO_2N\underline{H}_2$), 7.61–7.63 (s,d, 2H, Ar—$\underline{H}$) and 7.70 (bs, 1 H, Ar—$\underline{H}$);UV(EtOH) $\lambda_{max}$(e) 262.6 (20668), 208.6 (20726) and 204.6 (20527) nm; IR(KBr) 3326, 3229, 1693, 1489, 1325, 1186, 1046, 911, 828 and 768 cm$^{-1}$; FDMS(MeOH) m/e 270 (M$^+$).

Analysis for $C_{11}H_{14}N_2O_4S$: Theory: C, 48.88; H, 5.22; N, 10.36. Found: C, 49.08; H, 5.40; N, 10.56.

N-methyl-indoline-5-sulfonamide

A 3-liter, 3-neck flask with mechanical stirrer and nitrogen purge line was charged with ethyl-indoline-1-carboxylate-5-sulfonamide (27 g, 100 mmoles), as prepared supra, and 1000 ml of anhydrous tetrahydrofuran. Under nitrogen purge was then added lithium aluminum hydride (95%, 10 g, 250 mmoles) in portions over 20 minutes, resulting in strong exotherms. The reaction was stirred at room temperature and monitored using HPLC (reverse-phase, 40/60/0.2% acetonitrile/water/phosphoric acid, 1 ml/min, monitoring at 254 nm). After 2 hours the mixture was cooled in an ice-bath and carefully quenched by the addition of ice until no further reaction was noted. Concentrated hydrochloric acid (65 ml) was next added until the pH equaled 3. The inorganic solids were removed by filtration and the filtrate evaporated to give a tan solid (23 g). Purification was effected by slurrying the crude solid in 250 ml of $H_2O$ for 30 minutes and filtering, followed by rinsing of the cake with $H_2O$ (300 ml) and diethyl ether (300 ml). Vacuum drying gave 17.3 g (81%) of product sulfonamide. Recrystallization from methanol gave an analytical sample.

Analysis of the product gave the following results: mp=176–177° C.; $R_f$(1/1 EtOAc/hexane)=0.29; $^1$H NMR (300 MHz, $d_6$-DMSO) δ2.74 (s 3H, NC$\underline{H}_3$), 2.92 (t, 2H, J=8.4 Hz, CH$_2$C$\underline{H}_2$), 3.38 (t, 2H, J=8.4 Hz, CH$_2$C$\underline{H}_2$), 6.47 (d, 1H, J=8.3 Hz, Ar—$\underline{H}$), 6.91 (bs, 2H, exchanges with $D_2O$, $SO_2N\underline{H}_2$), 7.39 (s, 1H, Ar—$\underline{H}$) and 7.44 (d, 1H, J=8.3 Hz, Ar—$\underline{H}$); IR(KBr)3314, 3239, 1605, 1509, 1313, 1170 and 1062 cm$^{-1}$; FDMS(MeOH) m/e 212 (M$^+$).

Analysis for $C_9H_{12}N_2O_2S$: Theory: C, 50.92; H, 5.70; N, 13.20. Found: C, 50.87; H, 5.62; N, 12.91.

N-[[(3,4-dichlorophenyl)amino]carbonyl]-2,3-dihydro-1-methyl-1H-indole-5-sulfonamide To a solution of N-methyl-indoline-5-sulfonamide (16.0 g, 75 mmoles) in 75 ml of 1N aqueous sodium hydroxide and 75 ml of acetone was added, dropwise, a solution of 3,4-dichlorophenylisocyanate (97%, 14.6 g, 75.3 mmoles) in 70 ml of acetone over 10 minutes. Two hours later the mixture was filtered and the filtrate treated with 125 ml of 1N aqueous hydrochloric acid. The resulting solid was collected by filtration and rinsed with 100 ml of H$_2$O and then slurried in 200 ml of ethanol/water (1/1) for 1 hour. Filtration, followed by washing (100 ml of ethanol followed by 200 ml of diethyl ether) and vacuum drying gave 19.7 grams of the purified title compound, a yield of 65%.

Analysis of the product gave the following results: mp=174–176° C.; R$_f$(1/9 MeOH/CHCl$_3$)=0.40; $^1$H NMR (300 MHz, d$_6$-DMSO) δ2.77(s, 3H, NC$\underline{H}_3$), 2.96 (t, 2H, J=8.4 Hz, CH$_2$C$\underline{H}_2$), 3.44 (t, 2H, J=8.4 Hz, CH$_2$C$\underline{H}_2$), 6.48 (d, 1H, J=8.4 Hz, Ar—$\underline{H}$), 7.25 (d, 1H, J=8.8 Hz, Ar—$\underline{H}$), 7.46 (s, 1H, Ar—$\underline{H}$), 7.49 (s, 1H, Ar—$\underline{H}$), 7.58 (d, 1H, J=8.4 Hz, Ar—$\underline{H}$), 7.58 (s, 1H, Ar—$\underline{H}$)8.96 (s, 1H, exchanges with D$_2$O, N$\underline{H}$) and 10.57 (bs, 1H, exchanges with D$_2$O, SO$_2$N$\underline{H}$); IR(KBr) 3352, 3274, 1710, 1610, 1525, 1458, 1322 and 1040 cm$^{-1}$; FDMS (MeOH) m/e 399, 401 (M$^+$).

Analysis for C$_{16}$H$_{15}$Cl$_2$N$_3$O$_3$S: Theory: C, 48.01; H, 3.78; N, 10.50. Found: C, 48.05; H, 3.92; N, 10.46.

EXAMPLE 10

Preparation of 4-methyl-N-[[(4-trifluoromethylphenyl)amino]carbonyl]benzenesulfonamide

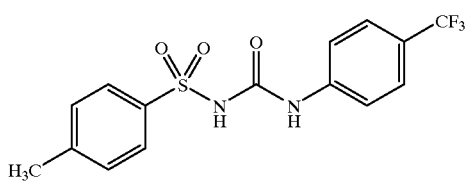

A solution of 8.0 g (49.65 mmoles) of 4-aminobenzotrifluoride in 10 ml of methylene chloride was added to a solution of 9.85 g (49.95 mmoles) of p-toluenesulfonyl isocyanate in 75 ml of methylene chloride with stirring. The mixture became quite warm and a heavy white precipitate formed. An additional 100 ml of methylene chloride were added. The reaction mixture was stirred an additional 15 minutes, and the precipitate was recovered by filtration affording 15.0 g of the title product as a white solid. A small amount of the material was crystallized from diethyl ether to provide the title compound (87% yield) with a melting point of 194–197° C.

Analysis for C$_{15}$H$_{13}$F$_3$N$_2$O$_3$S: Theory: C, 50.25; H, 3.66; N, 7.82. Found: C, 50.02; H, 3.63; N, 7.79.

EXAMPLE 11

Preparation of N[[(4-chlorophenyl)amino]carbonyl]-1,3-benzodioxole-5-sulfonamide

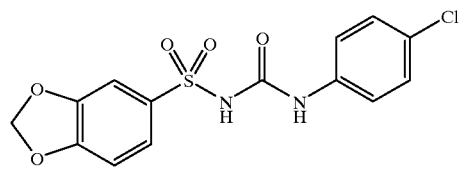

Preparation of 1,3-benzodioxole-5-sulfonamide

A 500 ml 3-neck round bottom flask was charged with 38.7 g (0.52 mole) of dimethylformamide. The contents of the flask were cooled to 0° C. After cooling, 70.18 g (0.52 mole) of sulfuryl chloride were added and the contents of the flask stirred for 10 minutes while maintaining the temperature at approximately 10° C.

After the Villsmeier reagent was formed, 60.16 g (0.5 mole) of 1,3-benzodioxole were added over a period of about 5 minutes. The mixture was heated to 80° C. for approximately 10 minutes. The temperature was increased to 110° C. and maintained for 5 minutes. The reaction mixture was allowed to cool to 40° C. and poured into a mixture of 450 g crushed ice, 200 ml water, and 200 ml of chloroform.

The resulting organic layer was decanted and then dripped into 200 ml of concentrated ammonium hydroxide. The solution was stirred for about 1.5 hours. After stirring, the organic and aqueous layers were allowed to separate and a yellow granular precipitate formed at the interface of the two layers. This solid was collected by filtration, washed with 100 ml of water, and dried overnight at 40° C. to provide 26.9 g of the desired subtitle intermediate.

Preparation of N[[(4-chlorophenyl)amino]carbonyl]-1,3-benzodioxole-5-sulfonamide To a solution of 26.9 g of 1,3-benzodioxole-5-sulfonamide in 100 ml of acetone was added 150 ml of a 1 N sodium hydroxide solution. A solution of 26.4 g of 4-chlorophenylisocyanate in 85 ml of acetone was added to the reaction mixture with stirring. After stirring at room temperature for 18 hours, the reaction mixture was filtered and 150 ml of 1 N hydrochloric acid were added to the filtrate, thereby providing a precipitate. One liter of water was added, and the solid was recovered by filtration to provide the desired title product in 75% yield.

EXAMPLE 12

Preparation of N-[5-(2,3-dihydrobenzofuryl)sulfonyl]-N'-(3,4-dichlorophenyl)urea

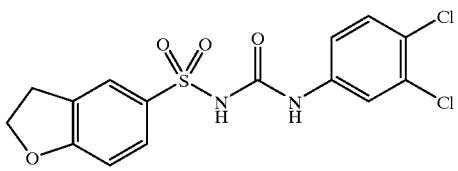

2,3-Dihydrobenzofuran-5-sulfonamide

This compound was prepared essentially according to the teachings of J. A. Aikins, et al., European Patent Publication 254,577, published Jan. 27, 1988. N,N-dimethylformamide (23.0 ml, 297 mmol) was cooled in an ice-salt bath and treated dropwise with sulfuryl chloride (20.0 g, 148 mmol) at such a rate that the reaction temperature was maintained below 15° C. To this was added 2,3-dihydrobenzofuran (17.0 g, 142 mmol), and after warming to room temperature, the reaction mixture was rapidly heated to 130° C. over ten minutes, and then allowed to cool to room temperature. The reaction mixture was poured into water/ice/dichloromethane, 1/5/1 (700 ml), and the organic layer collected. The aqueous layer was diluted with water (100 ml) and extracted with dichloromethane. The combined organic phase was dripped into an ammonium hydroxide solution (3N, 250 ml), and allowed to stir overnight. Residual dichloromethane was removed by distillation and the resulting solid collected on a filter, washed with a small amount of water, followed by ether and then dried by aspiration to provide 12.8 g (45%) of the product.

Analysis of the product gave the following results: mp=163–164.5° C.; $^1$H NMR (300 MHz, $d_6$-DMSO) δ3.21 (t, 2H, J=8.8 Hz, C$\underline{H}_2$), 4.60 (t, 2H, J=8.8 Hz, C$\underline{H}_2$), 6.86 (d, 1H, J=8.4 Hz, Ar—$\underline{H}$), 7.12 (bs, 2H, exchanges with D$_2$O, SO$_2$N$\underline{H}_2$), 7.56 (d, 1H, J=8.4 Hz, Ar—$\underline{H}$), 7.64 (s, 1H, Ar—$\underline{H}$); IR(KBr) 3356, 3255, 1606, 1590, 1557, 1407, 1442, 1314, 1249, 1149, 1116, 1070, 982, 923 and 836 cm$^{-1}$; FDMS(MeOH) m/e 200 (M$^+$).

Analysis for C$_8$H$_9$NO$_3$S: Theory: C, 48.23; H, 4.55; N, 7.03; S, 16.09. Found: C, 48.01; H, 4.71; N, 7.00; S, 16.36.

N-[5-(2,3-dihydrobenzofuryl)sulfonyl]-N'-(3,4-dichlorophenyl)urea

A solution of 2,3-dihydrobenzofuran-5-sulfonamide (29.6 g, 148.6 mmol) in acetone (75 ml) and 1N aqueous NaOH (150 ml, 150 mmol) was treated dropwise with a solution of 3,4-dichlorophenylisocyanate (30.0 g, 154.8 mmol) in 75 ml of acetone over 20 minutes. After stirring two hours, the insoluble bis(3,4-dichlorophenyl)urea was removed by filtration and the resulting clear solution neutralized by the addition of 1N aqueous HCl (150 ml, 150 mmol). The slurry was stirred 30 minutes, filtered and washed with water (500 ml), ether (200 ml), ether/hexane (1/1, 100 ml) and hexane (200 ml). Vacuum drying gave 50.1 g of crude product which was slurried in ethanol (300 ml) for one hour, collected on a filter and washed with ether. This ethanol reslurry was repeated and provided 42.7 g (74%) of the title compound after vacuum drying (50° C.).

Analysis of the product gave the following results: mp=188–189° C.; $^1$H NMR (300 MHz, $d_6$-DMSO) δ3.25 (t, 2H, J=8.8 Hz, C$\underline{H}_2$), 4.63 (t, 2H, J=8.8 Hz, C$\underline{H}_2$), 6.92 (d, 1H, J=8.6 Hz, Ar—$\underline{H}$), 7.25 (dd, 1H, J=2.5, 8.8 Hz, Ar—$\underline{H}$), 7.48 (d, 1H, J=8.8 Hz, Ar—$\underline{H}$), 7.68 (d, 1H, J=2.5 Hz, Ar—$\underline{H}$), 7.71 (d, 1H, J=8.5 Hz, Ar—$\underline{H}$), 7.77 (s, 1H, Ar—$\underline{H}$), 9.08 (s, 1H, exchanges with D$_2$O, ArN$\underline{H}$), 10.85, (bs, 1H, exchanges with D$_2$O, SO$_2$N$\underline{H}$); IR(KBr) 3275, 1701, 1580, 1511, 1452, 1380, 12444, 1202, 1142, 1115, 1045, 896, 708 and 585 cm$^{-1}$; FDMS (MeOH) m/e 386, 388, 390 (M$^+$).

Analysis for C$_{15}$H$_{12}$Cl$_2$N$_2$O$_4$S: Theory: C, 46.53; H, 3.12; N, 7.23. Found: C, 46.77; H, 3.24; N, 7.26.

EXAMPLE 13

Preparation of N-[[(4-chlorophenyl)amino]carbonyl]-4-methylbenzenesulfonamide

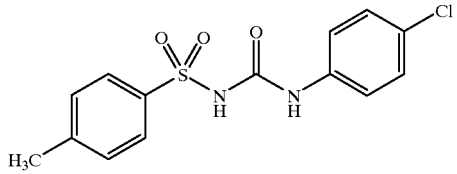

A solution of 6.25 g (49.00 mmoles) of 4-chloroaniline in 10 ml of methylene chloride was added to a solution of 9.85 g (49.95 mmoles) of p-toluenesulfonyl isocyanate in 75 ml of methylene chloride with stirring. The mixture became quite warm and a heavy white precipitate formed. An additional 100 ml of methylene chloride were added. The reaction mixture was stirred an additional 15 minutes, and the precipitate was recovered by filtration affording 15.0 g of the title product as a white solid. A small amount of the material was crystallized from diethyl ether to provide the title compound (87% yield) with a melting point of 174–176 C.

Analysis for C$_{14}$H$_{13}$ClN$_2$O$_3$S: Theory: C, 51.77; H, 4.03; N, 8.63. Found: C, 51.90; H, 4.08; N, 8.67.

EXAMPLE 14

Preparation of N-[[(4-chlorophenyl)amino]carbonyl]-indan-5-sulfonamide

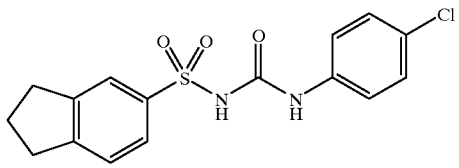

To a mixture of 93.2 g of indane-5-sulfonamide in 300 ml of acetone were added 490 ml of 1 N sodium hydroxide. A solution of 79.36 g of 4-chlorophenylisocyanate in 250 ml of acetone was added to the reaction mixture with stirring. After stirring at room temperature for about 18 hours, the reaction mixture was filtered and 490 ml of 1 N hydrochloric acid were added to the filtrate, thereby providing a fine white precipitate. One liter of water was added, and the solid was recovered by filtration to provide 144.86 g of the desired title product. m.p. 169–172° C.

Analysis for C$_{16}$H$_{15}$ClN$_2$O$_3$S: Theory: C, 54.78; H, 4.31; N, 7.79. Found: C, 54.95; H, 4.43; N, 7.94.

EXAMPLE 15

Preparation of N-[[(4-chlorophenyl)amino]carbonyl]-4-(ethenyl)benzenesulfonamide.

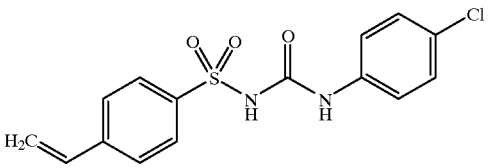

To a solution of 4-vinylbenzenesulfonamide, prepared essentially as described in R. H. Wiley, et al., *Journal of the American Chemical Society*, 78:2169 (1956), (5.1 g, 28 mmol) in 1 N aqueous sodium hydroxide solution (28 ml) and acetone (14 ml) was added, dropwise, a solution of 4-chlorophenylisocyanate (4.3 g, 28 mmoles) in acetone (14 ml) over 10 minutes. Two hours later the mixture was filtered and the filtrate treated with 1N hydrochloric acid (28 ml). The resulting solid was collected by filtration and rinsed with water (100 ml). The crude product was purified by dissolving in 100 ml water containing 40 ml 1N sodium hydroxide, followed by filtration of insoluble material and neutralization with 40 ml 1N hydrochloric acid. After filtration and washing (200 ml of water), vacuum drying gave 4.9 g (52%) of the purified title sulfonylurea.

Analysis of the product gave the following results: mp=182–184° C.; R$_f$(9/1, CHCl$_3$/MeOH)=0.30; $^1$H NMR (300 MHz, $d_6$-DMSO) δ5.45 (d, 1H, J=10.9 Hz, C$\underline{H}$), 5.98 (d, 1H, J=17.6 Hz, C$\underline{H}$), 6.83(dd, 1H, J=10.9, 17.6 Hz, C$\underline{H}$), 7.2–7.4 (m, 4H, Ar—$\underline{H}$), 7.68 (d, 2H, J=8.3 Hz, Ar—$\underline{H}$), 7.89 (d, 2H, J=8.3 Hz, Ar—$\underline{H}$), 9.0 (s, 1H, exchanges with D$_2$O, N$\underline{H}$) and 10.9 (bs, 1H, exchanges with D$_2$O, SO$_2$N$\underline{H}$); IR(KBr) 3360, 1710, 1604, 1542, 1462, 1340, 1161, 1034 and 927 cm$^{-1}$; UV(EtOH) λ$_{max}$(ε) 251.2 (33271) and 204.4 (36099) nm; FDMS (MeOH) m/e 336, 338(M$^+$).

Analysis for $C_{15}H_{13}ClN_2O_3S$: Theory: C, 53.49; H, 3.89; N, 8.32. Found: C, 53.54; H, 3.96; N, 8.19.

EXAMPLE 16

Preparation of N-[[(3,4-dichlorophenyl)amino]carbonyl]-4-(ethenyl)benzenesulfonamide.

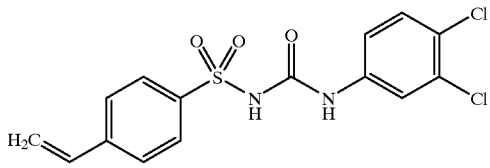

The procedure of Example 15 was followed, using 4-vinylbenzenesulfonamide (10 g, 55 mmoles), 1N sodium hydroxide (55 ml) and 3,4-dichlorophenylisocyanate (97%, 11 g, 55 mmoles). The crude product was purified by stirring in ethanol (50 ml) for 30 minutes, followed by filtration and vacuum drying to give 8.4 g (41%) of the title sulfonylurea.

Analysis of the product gave the following results: mp=179° C.; $R_f$(9/1, $CHCl_3$/MeOH)=0.24; $^1H$ NMR (300 MHz, $d_6$-DMSO) δ5.45 (d, 1H, J=10.9 Hz, C$\underline{H}$), 5.98 (d, 1H, J=17.6 Hz, C$\underline{H}$), 6.83(dd, 1H, J=10.9, 17.6 Hz, C$\underline{H}$), 7.25 (m, 1H, Ar—$\underline{H}$), 7.43 (d, 1H, J=8.7 Hz, Ar—$\underline{H}$), 7.6–7.7 (m, 3H, Ar—$\underline{H}$), 7.86 (d, 2H, J=8.7 Hz, Ar—$\underline{H}$), 9.1 (s, 1H, exchanges with $D_2O$, N$\underline{H}$) and 11.0 (bs, 1H, exchanges with $D_2O$, $SO_2N\underline{H}$); IR(KBr) 3347, 3250, 1710, 1589, 1521, 1464, 1338, 1161, 1040 and 843 cm$^{-1}$; UV(EtOH) $\lambda_{max}$(ε) 254.0 (33940) and 209.6 (41966) nm; FDMS (MeOH) m/e 370, 372, 374($M^+$).

Analysis for $C_{15}H_{12}Cl_2N_2O_3S$: Theory: C, 48.53; H, 3.26; N, 7.55. Found: C, 48.34; H, 3.29; N, 7.39.

EXAMPLE 17

Preparation of N-[[(4-chlorophenyl)amino]carbonyl]-3-(ethenyl)benzenesulfonamide.

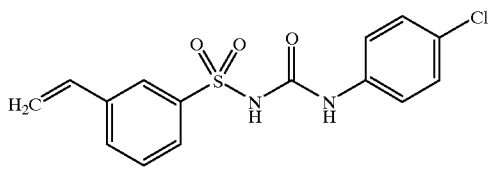

The 3-vinylbenzenesulfonamide was prepared by reacting a solution of 3-bromobenzenesulfonamide (24 g, 100 mmoles) with vinyltributyltin (97%, 35 ml, 116 mmoles) in the presence of tetrakis(triphenylphosphine)palladium(0) (2.3 g, 2 mmoles) in toluene (200 ml) and heated under nitrogen at reflux for 90 minutes. After cooling and filtering through Celite®, the reaction mixture was evaporated to yield 50 g of yellow solid. Chromatography (silica gel, 100% hexanes to 40% ethyl acetate/hexane) provided 5.2 g (28%) of the 3-vinylbenzenesulfonamide. Recrystallization from methanol gave an analytical sample.

Analysis of the product gave the following results: mp=131–132° C.; $R_f$(1/1, EtOAc/hexane)=0.48; $^1H$ NMR (300 MHz, $d_6$-DMSO) δ5.38 (d, 1H, J=10.9 Hz, C$\underline{H}$), 5.89 (d, 1H, J=17.6 Hz, C$\underline{H}$), 6.83(dd, 1H, J=10.9,17.6 Hz, C$\underline{H}$), 7.35 (s, 2H, $SO_2N\underline{H}_2$), 7.50 (m, 1H, Ar—$\underline{H}$), 7.7 (m, 2H, Ar—$\underline{H}$) and 7.89 (s, 1H, Ar—$\underline{H}$); IR(KBr) 3333, 3246, 1557, 1328, 1158, and 890 cm$^{-1}$; UV(EtOH) $\lambda_{max}$(ε) 297.8 (452), 288.6 (730), 280.8 (763), 248.2 (11423) and 214.8 (25659) nm; FDMS (MeOH) m/e 183($M^+$).

Analysis for $C_8H_9NO_2S$: Theory: C, 49.62; H, 4.95; N, 7.64. Found: C, 49.90; H, 4.61; N, 7.32.

The title compound was prepared essentially as described in Example 15, using the 3-vinylbenzenesulfonamide (3.0 g, 16.4 mmoles) prepared supra, 4-chlorophenylisocyanate (2.6 g, 16.6 mmoles) and 1N sodium hydroxide (16.4 ml). The crude product was chromatographed (silica gel, 1–5% methanol in methylene chloride) to give 2.7 g (49%) of N-[[(4-chlorophenyl)amino]carbonyl]-3-(ethenyl)benzenesulfonamide.

Analysis of the product gave the following results: mp=153–154° C.; $R_f$(9/1, $CHCl_3$/MeOH)=0.15; $^1H$ NMR (300 MHz, $d_6$-DMSO) δ5.38 (d, 1H, J=10.9 Hz, C$\underline{H}$), 5.89 (d, 1H, J=17.6 Hz, C$\underline{H}$), 6.83(dd, 1H, J=10.9,17.6 Hz, C$\underline{H}$), 7.25–7.40 (m, 4H, Ar—$\underline{H}$), 7.58 (m, 1H, Ar—$\underline{H}$), 7.78–7.85 (m, 2H, Ar—$\underline{H}$), 7.97 (s, 1H, Ar—$\underline{H}$), 9.1 (s, 1H, exchanges with $D_2O$, N$\underline{H}$) and 10.8 (bs, 1H, exchanges with $D_2O$, $SO_2N\underline{H}$); IR(KBr) 3329, 3239, 1705, 1598, 1534, 1456, 1337, 1158, 1038 and 927 cm$^{-1}$; UV(EtOH) $\lambda_{max}$(ε) 247.8 (32235) and 204.2 (35716) nm; FDMS (MeOH) m/e 336, 338 ($M^+$). Analysis for $C_{15}H_{13}ClN_2O_3S$: Theory: C, 53.49; H, 3.89; N, 8.32. Found: C, 53.45; H, 3.98; N, 8.20.

Preparation

Preparation of N-ethoxycarbonyl-4-hydroxy-3-(prop-2-en-1-yl)phenylsulfonamide

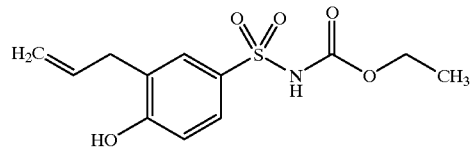

To a solution of 3-allyl-4-hydroxybenzenesulfonamide (2 g, 9.4 mM) [prepared as described in Patent Cooperation Treaty Publication WO 96/09818, published Apr. 4, 1996] in 100 ml methyl ethyl ketone was added potassium carbonate (1.4 g, 10 mM) and the mixture heated under nitrogen to reflux. After 10 minutes, ethyl chloroformate (1.8 ml, 18.8 mM, 2 equivalents) was added dropwise and the mixture refluxed for 3 hours. The cooled reaction was acidified with 1N hydrochloric acid (50 ml) and the layers separated. An additional wash with water (1×50 ml) and brine (1×24 ml), followed by drying over sodium sulfate and evaporation gave 3.3 g of the di-acylated product. The crude oil was dissolved in water (90 ml), 1N sodium hydroxide (29 ml) added and the mixture heated to reflux 2 hours. After cooling in an ice-bath, 1N hydrochloric acid (30 ml) was added and the resulting solid collected and dried to 1.87 g. Chromatography (silica gel, 100% methylene chloride to 5% methanol/methylene chloride) gave the product as a white solid, 1.3 g (49%).

Analysis of the title compound gave the following results: $R_f$(1/9 MeOH/$CHCl_3$)=0.29;

$^1H$ NMR (300 MHz, DMSO-$d_6$) δ1.05 (t, 3H, J=6.9 Hz, OC$H_2$C$\underline{H}_3$), 3.30 (d, 2H, J=6.7 Hz, C$\underline{H}_2$=CHC$\underline{H}_2$), 3.95 (q, 2H, J=6.9 Hz, OC$\underline{H}_2$C$H_3$) 5.05 (s, 1H, C$\underline{H}_2$=CHC$H_2$), 5.05 (d, 1H, J=4 Hz, C$\underline{H}_2$=CHC$H_2$), 5.85–5.94 (m, 1H, C$H_2$=C$\underline{H}$C$H_2$), 6.91 (d, 1H, J=8.4 Hz, Ar—$\underline{H}$), 7.50–7.60 (m, 2H, Ar—$\underline{H}$), 10.6(bs, 1H, exchanges with $D_2O$, OH), and 11.63 (bs, 1H, exchanges with $D_2O$, NH);

IR(KBr) 3409, 3212, 1728, 1592, 1488, 1425, 1366, 1348, 1290, 1239, 1159, 1129, 835 and 772 cm$^{-1}$;

UV(EtOH) λmax(ε) 244.5 (13070) and 207.0 (31769) nm;

FDMS (MeOH) m/e 285 ($^{M+}$).

Analysis for $C_{12}H_{15}NO_5S$: Theory: C, 50.52; H, 5.30; N, 4.91. Found: C, 50.39; H, 5.20; N, 4.66.

EXAMPLE 18

Preparation of N-[[[3,4-dichlorophenyl]amino]carbonyl]-4-hydroxy-3-(prop-2-en-1-yl)phenylsulfonamide

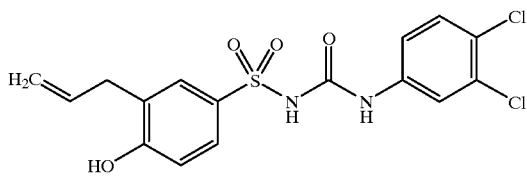

A solution of N-ethoxycarbonyl-4-hydroxy-3-(prop-2-en-1-yl)phenylsulfonamide (500 mg, 1.75 mM) and 3,4-dichloroanihne (340 mg, 2.06 mM, 1.2 equivalents) was prepared in toluene (25 ml) and heated to reflux under nitrogen, removing the toluene/ethanol azeotrope by use of a Dean-Stark trap. After 4.5 hour and removal of about 10 ml azeotrope, the solution was cooled in an ice-bath and the resulting precipitate collected and rinsed with cold toluene (10 ml). Vacuum dry to a white solid, 536 mg (76%).

Analysis of the title compound gave the following results:

$R_f$(1/9 MeOH/CHCl$_3$)=0.19;

$^1$H NMR (300 MHz, DMSO-d$_6$) δ3.31 (d, 2H, J=6.7 Hz, CH$_2$=CHC$\underline{H}_2$), 5.01 (s, 1H, C$\underline{H}_2$=CHCH$_2$), 5.06 (d, 1H, J=7.9 Hz, C$\underline{H}_2$=CHCH$_2$), 5.85–5.94 (m, 1H, CH$_2$=C$\underline{H}$CH$_2$), 6.91 (d, 1H, J=8.4 Hz, Ar—H), 7.22 (m, 1H, Ar—H), 7.45 (d, 1H, J=8.8 Hz, Ar—H), 7.50–7.65 (m, 3H, Ar—H), 9.03 (bs, 1H, exchanges with D$_2$O, CONH), 10.6 (bs, 1H, exchanges with D$_2$O, OH), and 10.8(bs, 1H, exchanges with D$_2$O, NH);;

IR(KBr) 3383, 3206, 1712, 1700, 1591, 1521, 1460, 1432, 1394, 1339, 1279, 1239, 1152, 1123, 1056, 864 and 706cm$^{-1}$;

FDMS (MeOH) m/e 400,402 (M$^+$, M$^+$+2).

Analysis for $C_{16}H_{14}Cl_2N_2O_4S$: Theory: C, 47.89; H, 3.52; N, 6.98. Found: C, 47.78; H, 3.61; N, 6.72.

The cystic fibrosis transmembrane conductance regulator (CFTR) is a chloride ion channel that is regulated by cAMP-dependent phosphorylation and by intracellular adenosine triphosphate. Intracellular ATP also regulates a class of potassium ion channels that have a distinctive pharmacology: they are inhibited by sulfonylureas and activated by a novel class of drugs termed potassium channel openers.

Mutations in a single gene encoding CFTR cause the disease cystic fibrosis. Amino acid sequence analysis and comparison with other proteins suggest that CFTR consists of five domains: two transmembrane domains, each composed of six transmembrane regions; an R domain, which contains several consensus sequences for phosphorylation by cAMP-dependent protein kinase; and two nucleotide binding domains which are predicted to interact with adenosine triphosphate. Such analyses suggest the CFTR belongs to a family of proteins that have been called the traffic ATPases. Some members of this family hydrolyze ATP to transport substrate across cell membranes.

EXAMPLE

The following examples show successful uses of CFTR chloride channel blockers as inhibitors of the chloride channels and certain cell lines. These assays are those employed in U.S. Pat. No. 5,234,922, issued Aug. 10, 1993, the entire contents of which are herein incorporated by reference. In particular for these studies NIH 3T3 fibroblasts are used that had been stably infected with a retrovirus expressing either wild-type human CFTR or a CFTR mutant in NBD2 (CFTR-K1250M, in which lysine 1250 is changed to methionine). Also employed is another transiently expressed mutant (CFTR-K-335E, in which lysine 335 in the first transmembrane domain is changed to glutamic acid) in HeLa cells using the vaccinia virus-T7 hybrid expression system. CFTR, in which part of the R domain is deleted (amino acids 708–835; CFTR DELTA R), is stably expressed in a mouse mammary cell line (C127 cells). This stable C127 cell line is generate by first inserting CFTR DELTA R cDNA in place of wild-type CFTR cDNA in a bovine papilloma virus (BPV)-based expression vector. The CFTR DELTA R plasmid is then introduced into C127 cells using calcium phosphate and transfectants are selected by neomycin resistance. Cells are maintained in culture. Patch pipettes are back-filled with an intracellular solution containing (mM): 120 N-methyl-D-glucamine, 85 aspartic acid, 3 MgCl$_2$, 1 CsEGTA (ethyleglycolbis-( beta -aminoethyl ether)N,N,N', N'-tetraacetic acid, cesium salt; Sigma Chemical Co., St. Louis, Mo.), 1 MgATP, and 5 TES (N-Tris(hydroxymethyl) methyl-2-aminoethane sulfonic acid), and pH is adjusted to 7.3 with HCl, yielding a Cl$^-$ concentration of 43 mM. By replacing K$^+$ in the intracellular solution with the impermeant cation N-methyl-D-glucamine, K$^-$-selective currents are inhibited. The free Ca$^{2+}$ concentration of the intracellular solution is <10$^{-8}$ M.

Cells are washed in Ca$^{2+}$- and Mg$^{2+}$-free phosphate-buffered saline and briefly treated with 0.25% (wt/vol.) trypsin to detach them from the plastic Petri dishes on which they are grown. This treatment did not affect the properties of CFTR Cl$^-$ currents. Small aliquots of cells are placed in a chamber (volume=0.5 cm$^3$) mounted on the stage of an inverted microscope and bathed in an extracellular solution containing (mM): 140 NaCl, 1.2 MgSO$_4$, 1.2 CaCl$_2$, 10 dextrose, and 10 TES (pH 7.3 with NaOH). Test solutions are gently perfused into the bath and removed by a vacuum pump. All solutions are filtered through 0.45-μm filters (Millipore Corp., Bedford, Mass.) and experiments are conducted at 34°–36° C. using a temperature controlled microscope stage (Brook Industries, Lake Villa, Ill.).

Patch pipettes are fabricated from thin-walled borosilicate glass capillary tubing (Rochester Scientific Co., Rochester, N.Y.) using a two-stage vertical pipette puller (model 750; David Kopf Instruments, Tujunga, Calif.) and coated with Sylgard (Dow Corning Corp., Midland, Mich.). Pipette tips are polished using a microforge. Patch pipettes had resistances of b 2–4 M OMEGA when filled with intracellular solution.

Whole-cell membrane currents are recorded using a List EPC-7 amplifier (List-Medical, Germany). Seals of 10–40 C OMEGA are routinely obtained. Cells are clamped at a holding potential of 0 mV and membrane currents are measured during depolarizing and hyperpolarizing voltage steps.

The established sign convention is used throughout. That is, ionic currents produced by positive charge moving from intra- to extracellular solutions (anions moving in the opposite direction) and shown as positive currents. The bath electrode consisted of an Ag—AgCl pellet connected to the bathing solution via an agar bridge filled with 1 M KCl.

A microcomputer and the pClamp software package (Axon Instruments, Inc., Foster City, Calif.) are used for pulse generation, data acquisition, and analysis. Voltage-pulse protocols are applied to the stimulus input of the List EPC-7 amplifier after digital-to-analog conversion using a TL-1 DMA interface (Axon Instruments, Inc.). The signal from the amplifier, which is filtered at 0.5–2.5 kHz using a variable 8-pole Bessel filter (Frequency Devices Inc., Haverhill, Mass.) is simultaneously viewed on a storage oscilloscope and acquired using pClamp software.

Adenosine trisphosphate magnesium salt (MgATT), 8-4-chlorophenylthio)-adenosine 3':5'-cyclic monophosphate sodium salt (CPT-cAMP), forskolin, 3-isobutyl-1-methylxanthine (IBMX), and TES are purchased from Sigma Chemical Co.

Stock solutions of the sulfonylureas and diazoxide are prepared in dimethyl sulfoxide and BRL 38227 in 70% (vol/vol) ethanol; minoxidil sulfate is prepared in acetone according to the manufacturer's instructions. Drugs are diluted in extracellular solution to achieve final concentrations at the time of use. The vehicle solutions did not affect CFTR Cl$^-$ currents (n=4 in each case).

Cells expressing CFTR exhibited little or no Cl selective current under baseline conditions. Addition of cAMP agonists (10 $\mu$M forskolin and 100 $\mu$M IBMX, or 500 $\mu$M CPT-cAMP, a membrane-permeant cAMP analogue) activated large Cl$^-$ selective currents. The current-voltage (I-V) relationship of the cAMP-regulated Cl$^-$ current is linear and the currents exhibited no evidence of voltage-dependent activation or inactivation. In preliminary experiments, CFTR Cl$^-$ current levels are stable over 3–5 min after activation.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid compositions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compositions may be administered, preferably orally or nasally, from devices which deliver the formulation in an appropriate manner.

The following examples illustrate the pharmaceutical compositions of the present invention.

Formulation Preparation 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient | 250.0 mg |
| Isotonic saline | 1000 ml |

Formulation Preparation 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

What is claimed is:

1. A method of treating secretory diarrhea in a mammal which comprises administering to a mammal in need thereof a therapeutically effective amount of a compound of the formula

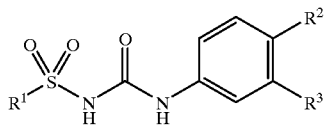

wherein:

$R^1$ is selected from the group consisting of

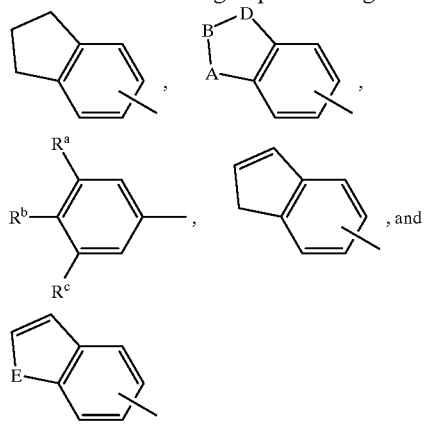

wherein:

E is nitrogen, sulfur, or oxygen;
where A is —O—, —S(O)$_n$—, —CH$_2$S(O)$_n$—, —NR—, —CH$_2$—, —CH$_2$CH$_2$—, or —CH$_2$O—;
D is —CH$_2$—, —S(O)$_n$—, —NR—, —CH$_2$S(O)$_n$—, or —O—;
B is —CH$_2$—, —O—, —S(O)$_n$—, or —NR—;
R is methyl or ethyl;
n is 0–2;
provided that at least one of A, B, and D is not —S(O)$_n$— or —CH$_2$S(O)$_n$—; and
$R^a$, $R^b$, and $R^c$ are independently selected from the group consisting of hydrogen, halo, $C_1$–$C_3$ alkyl $C_1$–$C_3$ alkoxy, and trifluoromethyl;
or one of $R^a$, $R^b$, and $R^c$ is $C_2$–$C_8$ alkenyl, another of $R^a$, $R^b$, and $R^c$ hydrogen or hydroxy, and the other of $R^a$, $R^b$, and $R^c$ is hydrogen;
$R^4$ and $R^5$ are independently selected from the group consisting of hydrogen and $C_1$–$C_3$ alkyl;
$R^3$ is hydrogen, halo, $C_1$–$C_3$ alkyl, or trifluoromethyl; and
$R^2$ is halo, $C_1$–$C_3$ alkyl, or trifluoromethyl;
or a pharmaceutically acceptable salt or solvate thereof.

2. A method as claimed in claim 1 employing a compound of the formula

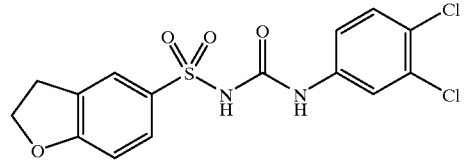

or a pharmaceutically acceptable salt or solvate thereof.

3. A method of treating cystic fibrosis in a mammal which comprises administering to a mammal in need thereof an effective amount of a compound of the formula

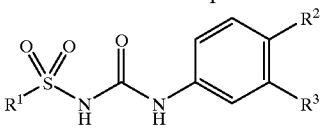

wherein:

$R^1$ is selected from the group consisting of

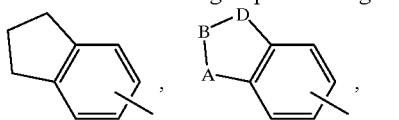

wherein:

E is nitrogen, sulfur, or oxygen;
where A is —O—, —S(O)$_n$—, —CH$_2$S(O)$_n$—, —NR—, —CH$_2$—, —CH$_2$CH$_2$—, or —CH$_2$O—;
D is —CH$_2$—, —S(O)$_n$—, —NR—, —CH$_2$S(O)$_n$—, or —O—;
B is —CH$_2$—, —O—, —S(O)$_n$—, or —NR—;
R is methyl or ethyl;
n is 0–2;
provided that at least one of A, B, and D is not —S(O)$_n$— or —CH$_2$S(O)$_n$—; and
$R^a$, $R^b$, and $R^c$ are independently selected from the group consisting of hydrogen, halo, $C_1$–$C_3$ alkyl, $C_1$–$C_3$ alkoxy, and trifluoromethyl;
or one of $R^a$, $R^b$, and $R^c$ is $C_2$–$C_8$ alkenyl, another of $R^a$, $R^b$, and $R^c$ hydrogen or hydroxy, and the other of $R^a$, $R^b$, and $R^c$ is hydrogen;
$R^4$ and $R^5$ are independently selected from the group consisting of hydrogen and $C_1$–$C_3$ alkyl;
$R^3$ is hydrogen, halo, $C_1$–$C_3$ alkyl, or trifluoromethyl; and
$R^2$ is halo, $C_1$–$C_3$ alkyl, or trifluoromethyl;
or a pharmaceutically acceptable salt or solvate thereof.

4. A method as claimed in claim 3 employing a compound of the formula

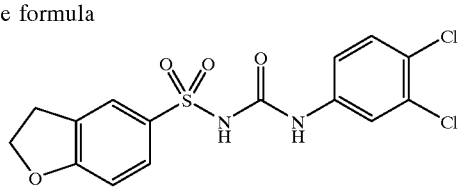

or a pharmaceutically acceptable salt or solvate thereof.

* * * * *